US00PP17192P2

(12) United States Plant Patent
Harris

(10) Patent No.: US PP17,192 P2
(45) Date of Patent: Nov. 7, 2006

(54) ***AZALEA* PLANT NAMED 'MNIESM'**

(50) Latin Name: ***Rhododendron* sp.**
Varietal Denomination: MNIESM

(76) Inventor: James O. Harris, 538 Swanson Dr., Lawrenceville, GA (US) 30043

( * ) Notice: Subject to any disclaimer, the term of this patent is extended or adjusted under 35 U.S.C. 154(b) by 31 days.

(21) Appl. No.: 11/180,479

(22) Filed: Jul. 13, 2005

(51) Int. Cl.
*A01H 5/00* (2006.01)

(52) U.S. Cl. ..... Plt./239

(58) Field of Classification Search ..... Plt./239, Plt./240
See application file for complete search history.

*Primary Examiner*—Kent Bell
(74) *Attorney, Agent, or Firm*—Jondle & Associates P.C.

(57) ABSTRACT

A new variety of *Azalea* plant found as a seedling in a planned cross between the female hybrid *Azalea* 'EMBERS' and the male hybrid *Azalea* 'September Morn' is disclosed. The new variety possesses a unique blooming time and is very cold hardy. It is an upright and slightly open growing *Azalea* with large and attractive, single to semi-double orange-red flowers.

3 Drawing Sheets

Genus/species: *Rhododendron* sp.
Botanical designation: 'MNIESM'.

BACKGROUND OF THE INVENTION

The present invention is a new and distinct variety of evergreen *Azalea* of the genus *Rhododendron.* This new *Azalea,* hereinafter referred to as 'MNIESM', was discovered in March, 1999 in Lawrenceville, Ga. 'MNIESM' originated from a cross between hybrid *Azalea* 'EMBERS' ('Conleb', U.S. Plant Pat. No. 10,581) and hybrid *Azalea* 'September Morn' (unpatented) in Lawrenceville, Ga. The value of this new cultivar lies in its unique blooming period, bloom color, bloom form, growth habit, and cold hardiness.

Asexual propagation of the new plant by cuttings was performed in Dearing, Ga. The new plant retains its distinctive characteristics and reproduces true to type in successive generations by vegetative propagation.

SUMMARY OF THE INVENTION

The following are the most outstanding and distinguishing characteristics of this new cultivar when grown under normal horticultural practices in Dearing, Ga.

1. Unique spring and fall blooming;
2. Attractive, showy, single/semi-double flower;
3. Easily propagated by semi-hardwood cuttings in late spring through summer;
4. Medium to fast growth rate under normal fertilization and moisture conditions;
5. Upright and slightly open nature;
6. Grows well in containers;
7. Thrives in shade or sun; and
8. Hardy in USDA Zone 6a.

DESCRIPTION OF THE PHOTOGRAPHS

This new *Azalea* hybrid variety is illustrated by the accompanying photographs which show blooms and foliage of the plant in full bloom. The colors shown are as true as can be reasonably obtained by conventional photographic means.

Figure 1:
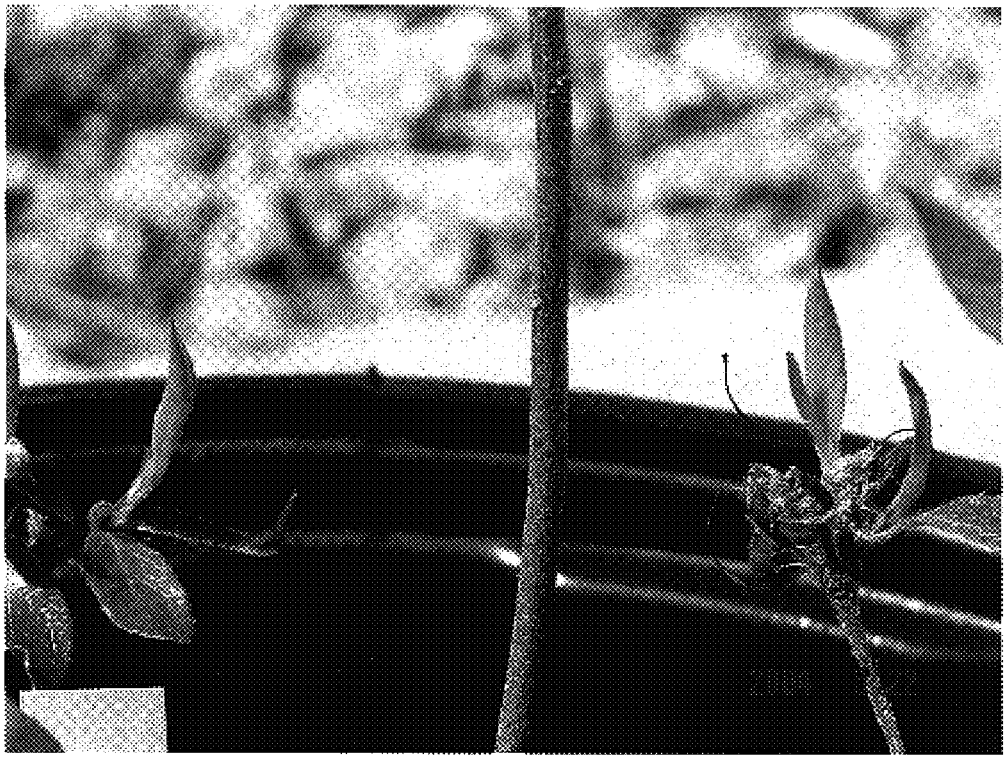

FIG. 1. shows a close-up view of a stem and immature foliage.

Figure 2:
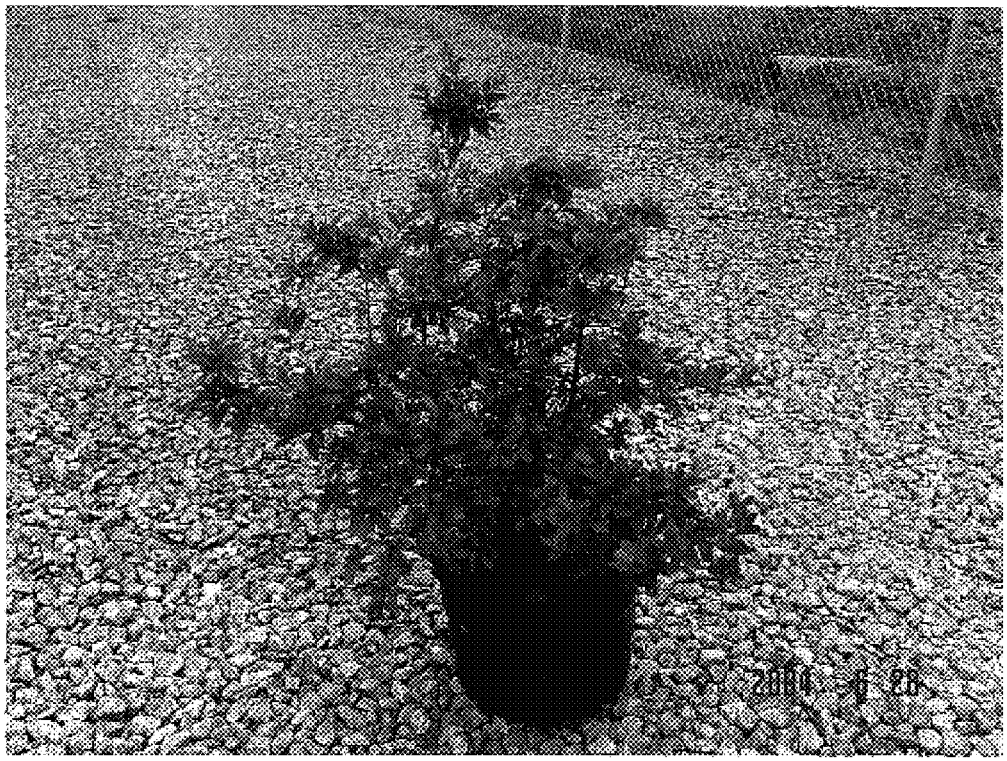

FIG. 2. shows mature foliage and growth habit of a seven-gallon plant.

Figure 3:
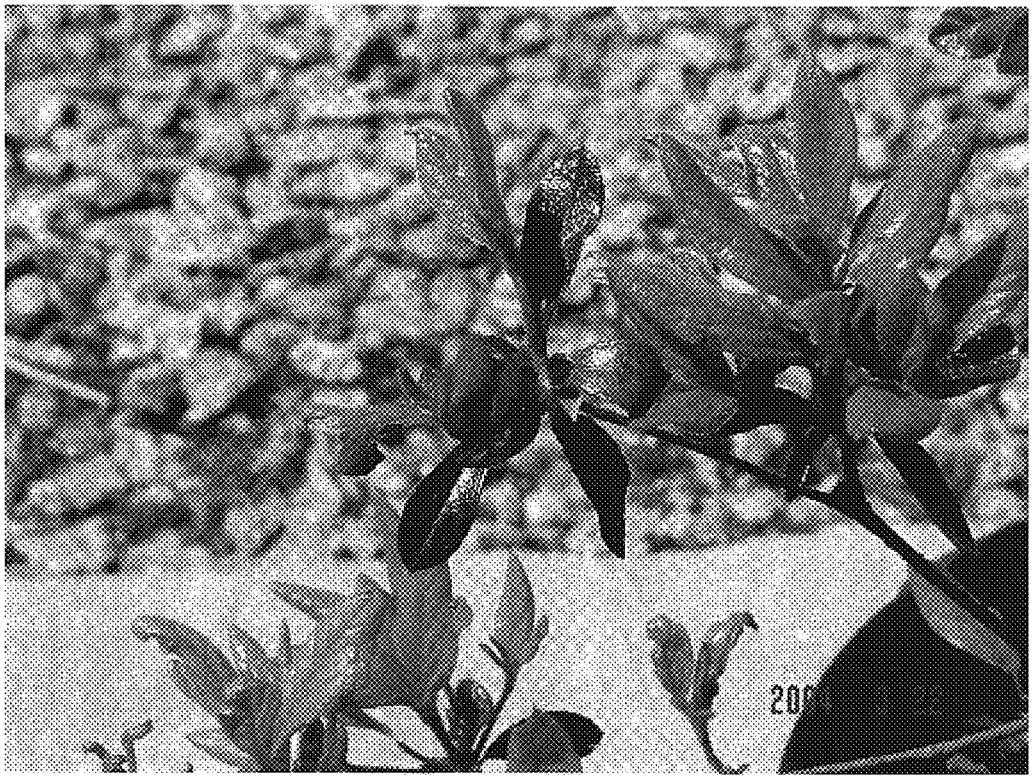

FIG. 3. shows a close-up view of a flower bud.

Figure 4:
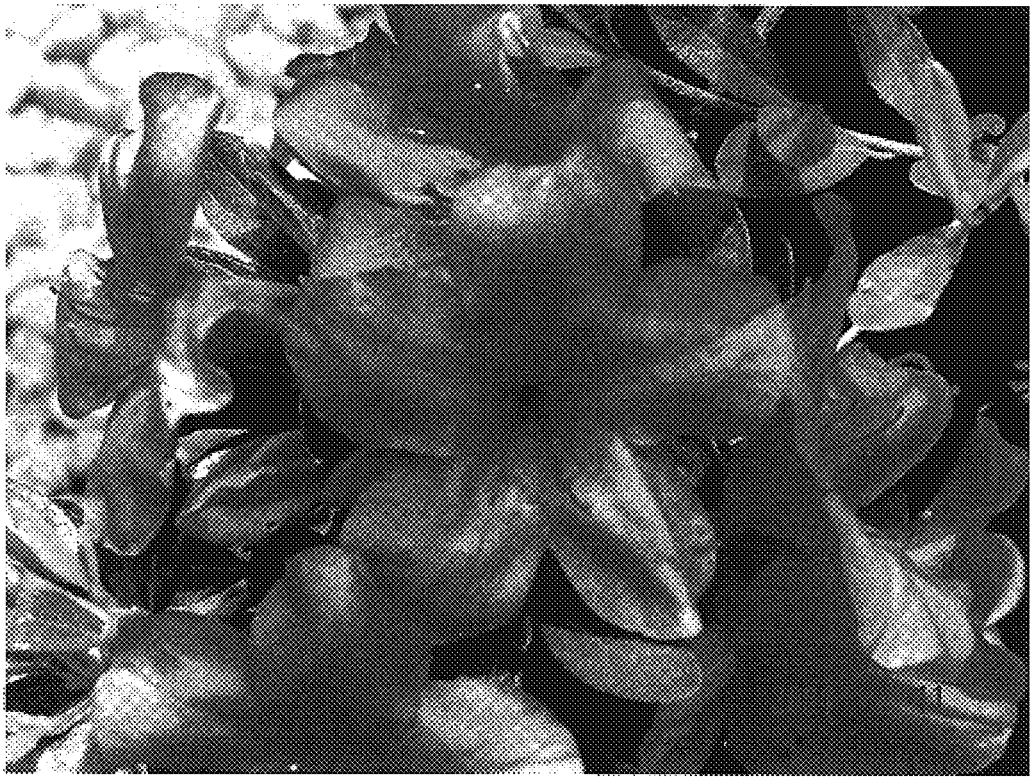

FIG. 4. shows several mature inflorescences.

Figure 5:
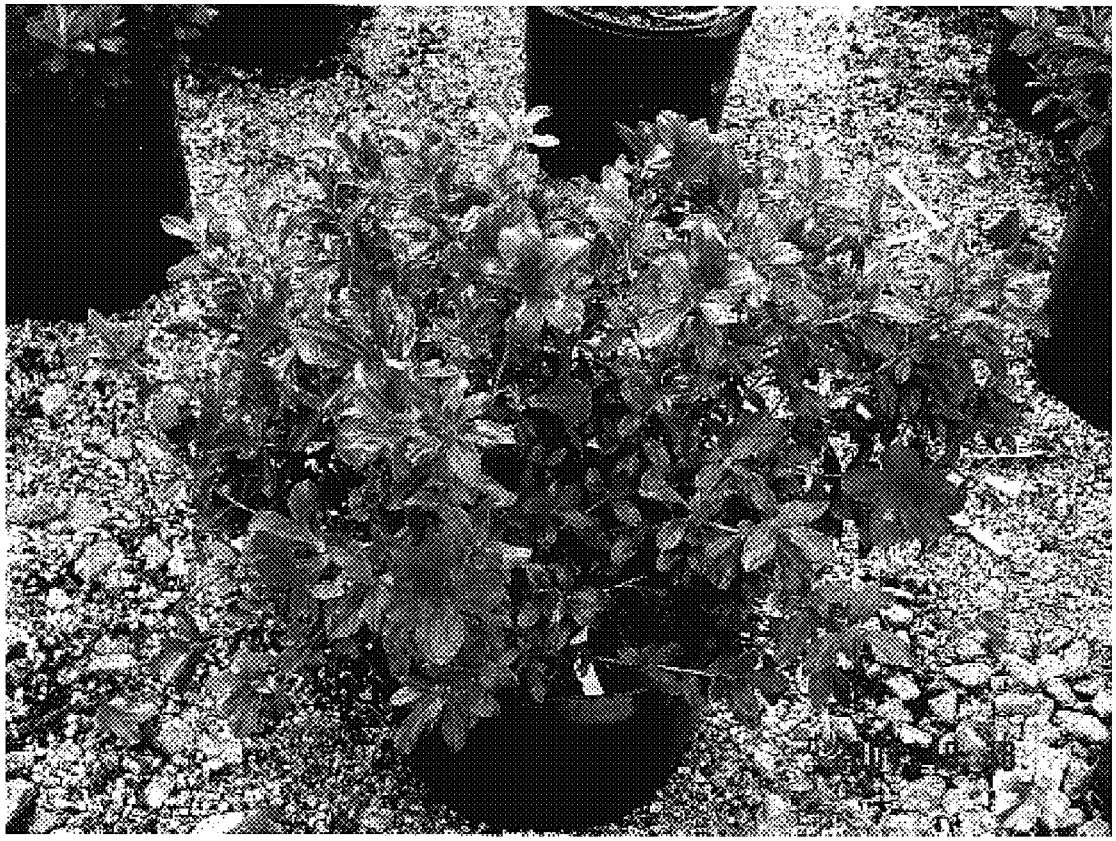

FIG. 5. shows the re-blooming characteristic of the plant.

DETAILED DESCRIPTION OF THE NEW PLANT

The following is a detailed description of the new variety of *Azalea* based on observations made of a 3 year-old plant grown in a seven-gallon container according to wholesale commercial production conditions in Dearing, Ga. The colors of the various plant parts are detailed with reference to The Royal Horticultural Society Colour Chart.

Classification:
*Family.*—Ericaceae.
*Species.*—*Rhododendron* sp.
*Common name.*—*Azalea.*
*Commercial name.*—'MNIESM'.

Parentage:
*Female parent.*—*Azalea* hybrid 'EMBERS' (U.S. Plant Pat. No. 10,581).
*Male parent.*—Harris hybrid *azalea* 'September Morn' (unpatented).

Growth:
*Form.*—Upright and globose.
*Height.*—9–15 inches.
*Width.*—2½ to 3 feet.
*Growth habit.*—Upright and slightly open.
*Growth rate.*—Medium to fast growth rate under normal fertilization and moisture conditions. In a period of six years from a rooted cutting, the plant reaches a height of 18–30 inches and a spread of 2½ to 3 feet. The growth rate is normally about 3 to 5 inches per year; the plant reaches a height of 36–60 inches at maturity.

*Spring growth.*—In 2004, the date of initial spring growth was March 17, in Dearing, Ga. After the initial spring flush, there was continuous growth through the fall. The average length of terminal growth of the initial spring flush is about 2¾ inches for a plant in full sun and about 2⅞ inches when grown in shade. This growth, if not pruned, will begin to produce flowers starting in April. As the plant continues to grow through summer and fall, more flower buds are produced which mature and bloom until frost. 'MNIESM' bloomed until frost in December. The remaining growth produces about 2 to 3 inches of new growth.

*Life cycle.*—Perennial, evergreen.

Leaves: Leaves are evergreen.

*Leaf arrangement.*—Alternate, simple.

*Leaf shape.*—Elliptic.

*Leaf length.*—2 inches.

*Leaf width.*—⅞ inches.

*Leaf margin.*—Entire.

*Leaf base.*—Cuneate.

*Leaf apex.*—Mucronate.

*Petiole length.*—¼ inch.

*Petiole color.*—RHS 145A (yellow-green).

*Mature leaf.*—Upper leaf surface: Surface texture: Semi-glossy. Surface color: RHS 137A (yellow-green). Surface pubescence: Strigose. Surface pubescence color: RHS 155C (white). Midveins and laterals: Impressed on surface. Lower leaf surface: Surface texture: Matte. Surface color: RHS 146B (yellow-green). Surface pubescence: Strigose. Surface pubescence color: RHS 155C (white). Midveins and laterals: Prominent on surface.

*Immature leaf.*—Upper leaf surface: Surface texture: Matte. Surface color: RHS 144A (yellow-green). Surface pubescence: Strigose and Scabrous. Surface pubescence color: RHS 164D (greyed-orange). Lower leaf surface: Surface texture: Matte. Surface color: RHS 144B (yellow-green). Surface pubescence: Strigose. Surface pubescence color: RHS 155C (white). Immature petioles and midveins: Petiole and midvein color: RHS 144C (yellow-green). Petiole and midvein pubescence: Strigose. Petiole and midvein pubescence color: RHS 155C (white). New growth pubescence: Strigose. Length of pubescence: 1/32 to 1/16 inch; numerous on mid-vein and petiole, more so as the leaf matures.

Stems:

*Young stems.*—Stem color: RHS 144B (yellow-green). Stem pubescence: Strigose. Stem pubescence color: at point of attachment hairs emerge RHS 155C (white) and mature to RHS 164B (greyed-orange); hairs distal from stem are RHS 164C (greyed-orange). Bark color of mature first-year stem: RHS199C (greyed-brown). Stem length: 2 to 5 inches. Stem diameter: 3/32 to ⅛ inch.

*Second-year stems.*—Bark color: RHS 199B to RHS 199C (greyed-brown). Stem pubescence: Glabrous. Stem length: 3 to 6 inches. Stem diameter: 3/16 inch.

*Pith.*—Solid and uniform.

*Internode length: Grown in full sun:* ⅛ inch to 1 inch; grown in light shade: ⅛ inch to ⅞ inch.

Flower buds:

*Buds.*—Tight; borne in groups of one to three; sheathed by a pair of modified leaf bracts.

*Bud shape.*—Ovate.

*Bud size.*—⅝×3/16 inch.

*Bud scales.*—Pubescent, individual hairs emerge RHS 155C (white) and mature to RHS 167C (greyed-orange).

*Bud color.*—RHS 142B (green).

*Bud sheath.*—Bud sheath length: 13/32 inch long, persistent. Immature sheath color: RHS 143B (green). Mature: As the buds swell, the bud sheath matures to RHS 144D (yellow-green) and RHS 53A (red), falls off, and reveals the flower color of RHS 34C (orange-red).

*Bud pedicel.*—Pedicel length: 7/16 inch long. Pedicel color: RHS 144A (yellow-green) and RHS 44D (red). Pedicel pubescence: Tomentose. Pedicel pubescence color: RHS N167C (greyed-orange).

*Calyx.*—Calyx shape: Cup-shaped, persistent. Size: ¼ inch long. Color: RHS 144A (yellow-green). Pubescence: Tomentose. Calyx pubescence color: RHS 155C (white).

Flowers:

*Flower type.*—Single to semi-double, perfect.

*Flowering habit.*—Borne on the current season's growth.

*Lastingness of flowers on the plant.*—4–7 days in the garden.

*Length of flowering period.*—2 to 3 weeks in April; flowering resumes in August and continues until frost, which can be as late as November or December in Dearing, Ga.

*Peduncle length.*—⅛ to ¼ inch.

*Shape.*—Open funnel-shaped.

*Flower diameter.*—2 to 2½ inches.

*Flower depth.*—2¾ inches.

*Petal number.*—5, fused at the base and remain fused up to ⅝ inch from the base.

*Petal pubescence.*—Glabrous.

*Petal shape.*—Obovate with rounded apices and undulate margins.

*Petal size.*—1⅝ inches long by 1 inch wide.

*Petal color.*—Upper and lower surfaces: RHS 34C (orange-red). Spots on 3 of the five petals: RHS 53A (red).

*Sepals.*—Ovate and joined at the base to form a cup.

*Sepal number.*—5.

*Sepal color.*—RHS 144A (yellow-green).

*Sepal size.*—¼ inch long×⅛ inch wide.

Reproductive organs:

*Ovary.*—Extremely tomentose.

*Placenta arrangement.*—5 locules.

*Pistil.*—Single, non-petaloid.

*Pistil length.*—1¾ to 1⅞ inches long.

*Stigma color.*—RHS 46A (red).

*Style color.*—RHS 45D (red).

*Stamen number.*—5, petaloid, some non-petaloid.

*Stamen length.*—1 1/16 to 1 3/16 inches.

*Stamen color.*—Filaments: RHS 47C to RHS 47D (red). Anthers: RHS 166C (greyed-orange).

*Pollen color.*—RHS 11D (yellow).

*Fragrance.*—None.

CULTURE

'MNIESM' grows well in a wide range of conditions and tolerates sun to shade. It prefers moist, well-drained soil that is rich in organic matter and responds well to mulching and medium applications of fertilizer. It does best in soil with a pH of 5.0 to 5.5. 'MNIESM' is adaptable to container and above ground planters; it also makes a good foundation plant or informal hedge with excellent foliage and flower contrast and requires very little pruning. It is propagated with semi-hardwood cuttings in late spring through the summer.

DISEASES/INSECTS

Lace bugs and spider mites can be a problem.

COMPARISON WITH PARENTAL CULTIVARS

The female, or seed parent, of 'MNIESM' is the hybrid *Azalea* 'EMBERS' (U.S. Plant Pat. No. 10,581) which has strong red, single/semi-double flowers, blooms both early and late seasons, and is a globose-shaped plant. 'EMBERS' is the result of a cross between the moderately pink Robin Hill hybrid *Azalea* 'Watchet' (unpatented) and the orange-red *Rhododendron oldhamii* 'Fourth of July' (unpatented).

The male, or pollen, parent is Harris hybrid 'September Morn' (unpatented). 'September Morn' is the result of a cross between the red blooming Gartrell hybrid 'Cherie' (unpatented) and the yellowish pink blooming Gable hybrid 'Indian Summer' (unpatented).

In Table 1 below, the instant plant is shown in comparison with the parental cultivars.

Example 9 (Enteric coated calcium polycarbophil formulation)

| Component | mg/tablet | Function |
|---|---|---|
| Core | | |
| Paroxetine Hydrochloride | 22.89* | Active |
| Calcium polycarbophil | 20.00 | Matrix |
| Lactose anhydrous | 146.11 | Hydrophilic agent/diluent |
| Polyvinylpyrrolidone | 10.0 | Binder |
| Magnesium stearate | 1.0 | Hydrophobic agent/lubricant |
| Water** | 0.024 | Granulating liquid |
| Enteric coat | | |
| Eudragit | 22.19 | Polymer |
| Talc | 1.53 | Lubricant |
| Triethyl citrate | 1.00 | Plasticizer |
| Water** | 24.6 | Diluent |
| Film coat | | |
| Opadry pink | 10.5 | Film coat |
| Water** | 94.5 | Diluent |
| Polish coat | | |
| Opadry clear | 0.750 | |
| Water** | 29.3 | Diluent |

*Equivalent to 20 mg paroxetine as free base.
**Removed during processing.

What is claimed is:

1. A new variety of *Azalea* plant named 'MNIESM' as herein shown and described.

* * * * *

UNITED STATES PATENT AND TRADEMARK OFFICE

CERTIFICATE OF CORRECTION

PATENT NO. : PP 17,192 P2
APPLICATION NO. :11/180479
DATED : November 7, 2006
INVENTOR(S) : James O. Harris It is certified that error appears in the above-identified patent and that said Letters Patent is hereby corrected as shown below:

Column 6, Table 1 reading
"Example 9 (Enteric coated calcium polycarbophil formulation)

| Component | mg/tablet | Function |
|---|---|---|
| Core | | |
| Paroxetine Hydrochloride | 22.89* | Active |
| Calcium polycarbophil | 20.00 | Matirx |
| Lactose anhydrous | 146.11 | Hydrophilic agent/diluent |
| Polyvinylpyrrolidone | 10.0 | Binder |
| Magnesium stearate | 1.0 | Hydrophobic agent/ lubricant |
| Water** | 0.024 | Granulating liquid |
| Enteric coat | | |
| Eudragit | 22.19 | Polymer |
| Talc | 1.53 | Lubricant |
| Triethyl citrate | 1.00 | Plasticizer |
| Water** | 24.6 | Diluent |
| Film coat | | |
| Opadry pink | 10.5 | Film Coat |
| Water** | 94.5 | Diluent |
| Polish coat | | |
| Opadry clear | 0.750 | |
| Water** | 29.3 | Diluent |

*Equivalent to 20 mg paroxetine as free base.
**Removed during processing" should read

UNITED STATES PATENT AND TRADEMARK OFFICE

CERTIFICATE OF CORRECTION

PATENT NO. : PP 17,192 P2
APPLICATION NO. :11/180479
DATED : November 7, 2006
INVENTOR(S) : James O. Harris It is certified that error appears in the above-identified patent and that said Letters Patent is hereby corrected as shown below:

Column 6, Table 1, should read

--

| Characteristic | 'MNIESM' | 'EMBERS' | 'September Morn' |
|---|---|---|---|
| Height (Mature) | 3 - 3½ ft. | 4 - 5 ft. | 2½ ft. |
| Width (Mature) | 2½ - 3 ft. | 5 - 6 ft. | 3 ft. |
| Flower Diameter | 2 - 2½ in. | 2½ - 2¾ in. | 2 - 2½ in. |
| Flower Form | Single/semi-double | Single/semi-double | Single |
| Flower Color | RHS 34C (red) | RHS 44A (red) | RHS 48A |
| Flowers per Terminal | 2 – 3 | 2 - 3 | 2 |
| Bloom Period | April; August to frost | April; Late July to frost | Early April; September to frost |
| Petal Number | 5-10 | 5 - 14 | 5 |
| Hardy Zone | 6 | 7 | 5 |
| Stamen Number | 0-5 | 0-9 | 5 |
| Stamen Type | Some petaloid | Some petaloid | Non-petaloid |

--.

Signed and Sealed this

Thirtieth Day of January, 2007

JON W. DUDAS
*Director of the United States Patent and Trademark Office*